United States Patent [19]

Kase et al.

[11] Patent Number: 4,631,857
[45] Date of Patent: Dec. 30, 1986

[54] FLOATING ARTICLE FOR IMPROVED CONTROL OF AQUATIC INSECTS

[75] Inventors: Lawrence E. Kase, Baltimore; Philip L. Branton, Fallston, both of Md.

[73] Assignee: Summit Chemical Company, Baltimore, Md.

[21] Appl. No.: 545,200

[22] Filed: Oct. 25, 1983

Related U.S. Application Data

[63] Continuation-in-part of Ser. No. 347,310, Feb. 9, 1982, abandoned.

[51] Int. Cl.$^4$ .............................................. A01M 1/20
[52] U.S. Cl. ...................................... 43/132.1; 43/131
[58] Field of Search ................ 43/131, 132.1; 424/21, 424/DIG. 9, DIG. 10

[56] References Cited

U.S. PATENT DOCUMENTS

| | | | |
|---|---|---|---|
| 2,109,642 | 3/1938 | Hunt | 43/124 |
| 3,127,235 | 3/1964 | Benzel | 210/764 |
| 4,166,112 | 8/1979 | Goldberg | 424/93 |
| 4,218,843 | 8/1980 | Clarke | 43/131 |
| 4,228,614 | 10/1980 | Cardarelli | 43/131 |
| 4,340,491 | 7/1982 | Lee | 43/124 |

OTHER PUBLICATIONS

Mosquito News vol. 9, No. 2, Observations on the use of Toxic Briquettes . . . , Raley & Davis.

Primary Examiner—Nicholas P. Godici
Assistant Examiner—K. Rowan
Attorney, Agent, or Firm—Leonard Bloom

[57] ABSTRACT

A molded non-layered unitary article (serving as a larvicide carrier) is formed solely from a substantially homogeneous mixture consisting of cork particles and a molding-type of plaster into which a larvicidal micro-organism, such as *B.t.i.*, has been added. The article may be dispensed conveniently, on to either small or large bodies of water, without regard for its orientation relative to the body of water. The article has a specific gravity of less than 1.0 and floats freely on the surface of the water, but if desired, may have a restrained-floating application. A sustained release of the larvicidal micro-organism is assured for effective mosquito control. All of the ingredients are found in nature, are bio-degradable, and are non-toxic to non-target organisms; hence will not adversely affect the environment. In a preferred embodiment, the article is substantially-toroidal and slightly-tapered and is provided with a central opening therein.

8 Claims, 12 Drawing Figures

*Fig. 1* — CARRIER OF A LARVICIDAL MICRO-ORGANISM

*Fig. 2* — MIXTURE OF CORK AND PLASTER

*Fig. 3* — FREE-FLOATING APPLICATION

*Fig. 4* — RESTRAINED-FLOATING APPLICATION

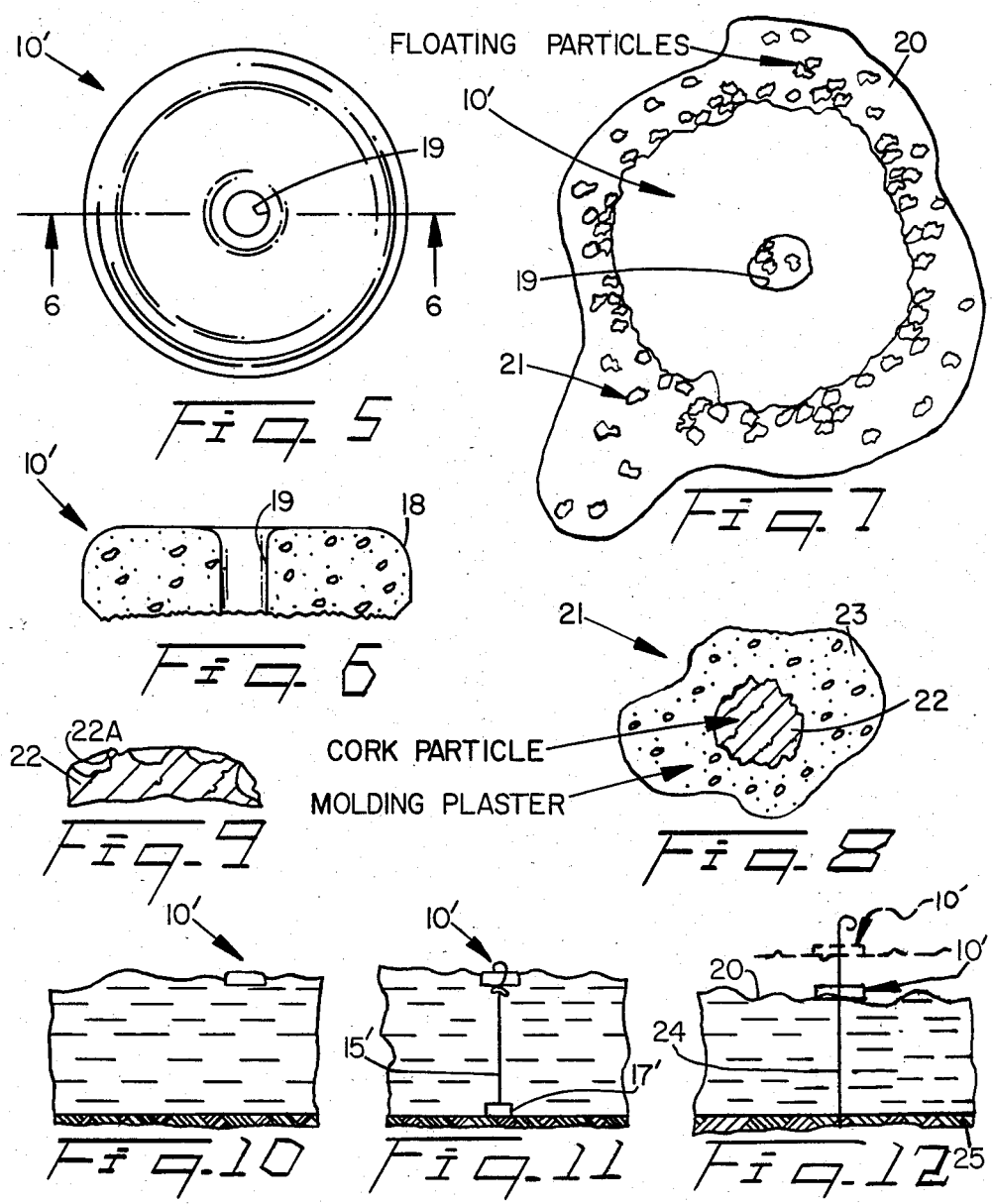

FLOATING ARTICLE FOR IMPROVED CONTROL OF AQUATIC INSECTS

CROSS-REFERENCE TO RELATED APPLICATIONS

This application is a continuation-in-part of application Ser. No. 347,310, filed Feb. 9, 1982 now abandoned, and entitled "Internal Flotation-System For Carrier of Larvicidal Micro-Organism For Insect Control", the disclosure of which is incorporated herein in its entirety by reference.

FIELD OF THE INVENTION

This invention relates to a floating article for improved control of aquatic insects, and more particularly, to a floating article containing a larvicidal micro-organism for the destruction of the mosquito larvae, black fly larvae, and the like.

BACKGROUND OF THE INVENTION

Mankind has for many years struggled against various insects, such as the mosquito and the black fly. These types of insects breed in various bodies of water, such as marshes, stagnant water, catch basins, ponds, woodland pools, abandoned pools and the like. Each adult female mosquito is capable of depositing hundreds of eggs, each of which experiences a complete metamorphosis. The egg hatches into a larva, and after a period of time, the larva enters into a pupa stage. The pupa stage is also spent in the water, and within a few days the adult mosquito emerges.

With respect to the commercial practices used in the field of mosquito control, and especially those intended for use primarily by governmental agencies and by large-scale industrial users, three "generations" of insecticides have been developed over the years. The first are various chemicals which are dispensed by foggers or sprayers, both on the ground and through the air. These chemicals may be classified as either adulticides or larvicides and are intended to attack and kill the adult mosquito or its larva, respectively. These chemicals usually have an inherent toxicity, which is potentially injurious to the environment, to marine life and wildlife, and ultimately to humans. As a result, these chemical insecticides have been viewed with disfavor in recent years.

One such product was "DURSBAN 10CR" produced by Dow Chemical Company around 1975. It was molded into the matrix of a polyethylene pellet, and the pellets were simply thrown into the water. Although the pellets sank to the bottom, the chemical larvicide was intended for a controlled release over a substantial duration. However, there were two problems with this product. First, it had an inherent toxicity problem which was potentially harmful to the environment. Second, and because of the long-term long-lasting effects of this product, the larvae could develop a resistance; and ultimately, the mosquitos could develop an immunity to adulticides of the same chemical family. This situation is referred to as "cross resistance" and illustrates that under adverse conditions, insects may tend to adapt. This ability to adapt, often within a few generations, can be somewhat exasperating for researchers engaged in the field of mosquito control.

As a departure from the chemical adulticides and larvicides, a second generation was developed. This second generation is known as insect growth regulators. Their purpose is to prevent the embryo from developing into an adult. The larva enters into its pupa stage but never develops into an adult. These products have very low toxicity, or practically no toxicity, and hence are not detrimental to marine life.

One such product is "ALTOSID" which is manufactured by Zoecon Corporation of Palo Alto, Calif. This product is available in two forms, one a liquid called "ALTOSID" SR-10, and the other a solid block called "ALTOSID" briquets. The active ingredient is methoprene. The methoprene is impregnated into a truncated cone-shaped charcoal briquet, and the briquets are sold as a package and are removed singly for individual use. The briquet is thrown into the water and sinks to the bottom. It decomposes slowly and is intended to have a sustained release over a period of about thirty days. During this time period, the briquets release the methoprene to prevent the mosquito larvae in the water from developing into adults. Because of the charcoal form of the briquet, it is messy and somewhat inconvenient to handle.

For about the past fifteen years, a third generation has been developed. Basically, these are bacteriological methods for spreading disease among insect populations. One of the most successful disease agents is *Bacillus thuringiensis* Berliner var. *kurstaki*, a bacterium which infects the larvae of Lepidoptera (moths) that are to be destroyed. More recently, a new variety has been uncovered for use against mosquito larvae and black fly larvae. This is *Bacillus thuringiensis* Berliner var. *israelensis* and its accompanying proteinaceous parasporal particles which contain protoxin. This bacillus is an aerobic spore-forming rod and is presently formulated into either a flowable liquid concentrate or a wettable powder, the latter being available commercially from Biochem Products under the trademark "BACTIMOS". The liquid concentrate or wettable powder is mixed with water and suspended, and the suspended particles are sufficiently fine to be sprayed homogeneously. Alternately, the *Bacillus thuringiensis* Berliner var. *israelensis* may be carried by granules of clay, sand, or other suitable granular material having a 20 to 40 mesh.

When these granules are used as a larvicidal carrier for either a chemical insecticide, an insect growth regulator, or a larvicidal micro-organism—a major problem is encountered. These granules have a specific gravity which is greater than water and thus sink towards the bottom of the water. Since the larvae breed at or near the surface of the water, much of the active larvicide is thus wasted. As a result, either the concentration of larvicide in the water is insufficient to destroy the mosquito larvae completely, or else a greater quantity of larvicide must be used to achieve the desired objective.

Moreover, when a larvicidal micro-organism of the bacillus type is used, and is sprayed on the water in the form of a liquid produced by diluting the wettable powder or liquid concentrate with water, a similar problem is encountered. The bacillus spores and protoxin particles are themselves heavier than water and sink towards the bottom. Additionally, the application of the bacillus does not have a sustained release—it is essentially "one shot"—and hence re-applications are often necessary to insure an effective mosquito control program. This is time consuming and expensive.

Besides these existing commercial practices, the prior art has disclosed various devices and methods for the control or destruction of mosquitos and other aquatic pests.

For example, the 1948 issue of MOSQUITO NEWS (vol. 9, No 2, pp. 68-71) disclosed a series of experiments conducted by Raley and Davis. These experiments and observations were made on behalf of the Consolidated Mosquito Abatement District, Fresno County, Calif. In the first experiment, a straight casting plaster was mixed with 25% emulsible DDT, the mixture was placed in a glass jar until semi-hard, and the jar was placed at the larvae source. The mixture disintegrated slowly, the DDT was not released rapidly, and this was unsatisfactory. Next, a mixture of casting plaster, sawdust, and a DDT derivative was formed into a briquet, and the briquet was placed in a perforated coffee can. This was an improvement, but still unsatisfactory, since the holes in the can became plugged in sources containing heavy organic matter. In a further step, the can was eliminated and the briquet was suspended on a wire. As reported, this worked satisfactorily in "quiet" water. However, fluctuations in the water level defeated the purpose of this fixed dispenser, and in several instances, the water level actually dropped below the suspended briquet. In an effort to correct this deficiency, the briquet was molded on a float consisting of a large wooden block. Several large-headed tacks or screws were set in the wooden block, the mold was placed around the tacks or screws, and the mixture was poured into the mold and allowed to harden.

The mixture used in the floating briquet disclosed in MOSQUITO NEWS consisted of equal parts of casting plaster and wood shavings. Apparently, this mixture (per se) would not float, or else the authors realized that sawdust will absorb moisture and eventually (if not quickly) sink towards the bottom of the body of water. Thus it was necessary to mold the mixture onto a separate layer consisting of a wood block, and to make this block substantially larger than the applied mixture in order to obtain the desired buoyancy. Moreover, the composite structure of this floating briquet would be position sensitive, that is, for maximum effect it should be carefully placed on the surface of the body of water so that the mixture containing the DDT would be below (rather than above) the wood block and hopefully remain in that position despite the turbulences in the water. Accordingly, this structure was not at all adaptable to random and convenient dispensing over various bodies of water, nor to large-scale production for commercial usage.

THE MOSQUITO NEWS publication (vintage 1948) specifically noted that the Consolidated Mosquito Abatement District consisted of a 1000 square mile area that must be regularly patrolled for mosquito sources; that this area included a vast number of small but prolific larvae hatching areas, and that it would be desirable to find a satisfactory method of larvae control other than spraying.

The general concept of floating devices or methods was also disclosed in the following U.S. Letters Patents:

No. 147,615 issued to Dayton in 1874 for an "improvement in disinfecting compounds"—this floating disinfectant consisted of sawdust dried, scorched, and treated successively with sulphate of iron and a volatile distillate of coal-tar—;

No. 2,468,394 issued to Dinsley in 1949 for a "carniverous fish repellent" in a dispersal container provided with a float composed of wood, plastic, kapuk, cork or other material; and No. 3,127,235 issued to Benzel in 1964 for a "method of forming and maintaining films on surfaces of liquids" for various purposes, including pesticides.

Moreover, in U.S. Letters Pat. No. 3,590,119 issued to Cardarelli et al in 1971, a "floating larvicide" was disclosed consisting of a delayed-release toxic substance dissolved into a molded elastomeric matrix. Pellets of the resulting composition (preferably in vulcanized form) were dispersed upon the infested water. In U.S. Letters Pat. No. 4,228,614 issued to Cardarelli in 1980, a "floating pesticide dispenser" was disclosed consisting of a slow release floating polymer for destroying aqueous pests, including mosquito larvae. The dispenser was in the form of a thin strip or tape of a polymer matrix, tethered to a suitable anchor, and comprising a copolymer of ethylene-vinyl acetate and/or an ethylene-propylene copolymer.

Furthermore, U.S. Letters Pat. Nos. 4,166,112 and 4,187,200 issued to Goldberg in 1979 and 1980, respectively, disclosed *Bacillus thuringiensis* in which a carrier was formulated as a buoyant colloidal suspension which stabilized just under the surface of the water.

According to information published by Biochem Products, a division of Salsbury Laboratories, Inc., a member of the Solvay Group, the earliest documented record of *Bacillus thuringiensis* was in Japan in 1901. In the decades since, at least 14 varieties of *B.t* have been identified from several countries on the bases of biochemical characteristics and serotyping of vegetative cell flagellar antigens. *Bacillus thuringiensis*, Berliner also known as HD-1, Serotype H-3a3b, or *B.t.* variety *kurstaki*, has been registered in the United States since 1961 for control of Lepidoptera larvae or caterpillars and is the type commonly used in forestry, agriculture, home and commercial gardening and horticulture. Products containing *B.t* reportedly have an excellent safety record with no documented incidents of serious or undesirable side effects on man and the environment. Biochem Products supplies a wettable powder or a flowable concentrate under the trademark "BACTIMOS". "BACTIMOS" is derived from *B.t.i.*, Serotype H-14, *Bacillus thuringiensis* variety *israelensis* which was discovered in Israel in 1976. This is a larvicidal micro-organism comprising *Bacillus thuringiensis* Berliner var. *israelensis* and its accompanying proteinaceous parasporal particles which contain protoxin (commonly referred to as "*B.t.i.*").

For mosquito control purposes, the BACTIMOS (*B.t.i.*) is invariably mixed with water and is applied to large areas, using airplanes or helicopters. This method of application has been continually used in the prior art, despite the constant and critical need for an alternate delivery system for the myriad of ponds and other small bodies of water, as recognized in MOSQUITO NEWS in 1948.

Moreover, any attempt to impregnate *B.t.i.* (or the larvicidal micro-organism of the aforesaid Goldberg patents) into the floating thermoplastic carrier of the aforesaid Cardarelli patent, would be impractical (if not impossible) and would destroy the stated utility of these references. An exposure of the *B.t.i.* particles to temperatures above 70° or 80° Centigrade—depending upon the exposure time, which is inversely correlated with temperature—will cause the *B.t.i.* to suffer a protein denaturization, resulting in a change in its molecular structure and losing its activity. Thus, it would be impractical to attempt to incorporate *B.t.i.* into a thermoplastic or elastomeric strip of material, in view of the molding temperatures likely to be encountered. Moreover, even if the *B.t.i.* could be incorporated into a polymer or elastomeric matrix without substantially limiting or destroying its very efficacy, these *B.t.i.* particles are agglomerations of relatively-large molecules and are incapable of migrating within a polymer or elastomeric matrix. Hence, they would not even be released, since the active protein toxin has a molecular weight of approximately 28 megadaltons.

Thus despite the deficiencies and disadvantages of the devices and systems resorted to in commercial practices in the field; despite the numerous floating devices long since disclosed in the prior art for the control of various aquatic pests; despite the relatively extensive research and patent activity in the field of mosquito control; despite the early recognized and long-felt need for a commercially-practical conveniently-dispensed device or delivery system (other than spraying) for launching an effective mosquito control program for the myriad of ponds and other small bodies of water; and despite the ready availability of larvicidal micro-organisms, such as *B.t.i.*—no one (prior to the applicants herein) has disclosed a completely satisfactory solution to this problem of long standing.

In an effort to solve this problem of long standing, and as disclosed in the applicants' copending application, Ser. No. 466,210 filed Feb. 14, 1983, which is a continuation of application Ser. No. 333,579 filed Dec. 22, 1981, which in turn is a continuation-in-part of application Ser. No. 300,013 filed Sept. 8, 1981, a package of individual briquets was developed for mosquito control purposes. Each briquet comprised two layers suitably joined to each other. One layer comprised a plaster base containing the *B.t.i.* or other larvicidal micro-organism, and the other layer comprised a closed cell polymer foam. The polymer foam provided the desired buoyancy to allow the layered biquet to float freely on the surface of the water. Since the dimensions (length and width) of the external foam float were substantially coterminous with the corresponding dimensions of the plaster carrier for the larvicidal micro-organism, the layered briquet was position "neutral" or insensitive; that is, the layered briquet could be simply thrown out over a body of water without regard to the orientation of the briquet relative to the surface of the water. Since the dimensions were substantially equal, and since the plaster layer was heavier than the foam layer, the layered briquet would invariably re-orient itself so that the foam layer was on the top and the plaster layer was on the bottom, whereby the plaster layer would gradually disintegrate or be eroded away for a sustained release of the larvicidal micro-organism over a sufficient period of time for effective mosquito control purposes.

While sufficient for the purposes intended, and while constituting an improvement in the art, these layered briquets nevertheless had some characteristics which interfered with full-scale commercial production. First, the separate layers required production methods which were somewhat tedious and archaic. Second, while a free-floating application was intended, there was no means for a restrained-floating application if desired by a particular mosquito-control agency. Third, the polymer foam float was not bio-degradable and thus was not completely compatible with the surrounding environment.

SUMMARY OF THE INVENTION

Applicants have discovered that the layered briquet concept—suggested in the art for thirty years and initially followed by the applicants—could be eliminated entirely in favor of a unitary non-layered molded article formed solely from a substantially homogeneous mixture consisting of granules of a buoyant material and a molding-type of material to which a larvicidal micro-organism has been added, wherein the article has a specific gravity of less than 1.0 and may be conveniently dispensed on to the surface of a body of water without regard for the orientation of the article with respect to the surface of the water, wherein the article will continue to float on the surface of the water where the larvae breed and will gradually disintegrate into a plurality of individual particles which will continue to float for a sustained release of the larvicidal micro-organism and over a relatively wide area of the surface where the larvae breed, and wherein all of the ingredients in the article are non-toxic to non-target organisms and will not adversely affect the environment. Additionally, all of the ingredients are found in nature and are biodegradable.

This discovery constitutes a quantum improvement in the art; it has met with immediate acceptance in the field and has proven to be effective for destroying the larvae of aquatic insects, and more specifically, the mosquito larvae.

In a preferred embodiment, the article has a substantially-toroidal slightly-tapered shape and is formed with a central bore, whereby, if desired, the article may be secured or else tethered in a restrained-floating application.

The buoyant material preferably comprises cork granules. When the article disintegrates, a plurality of individual floating "satellites" or particles are formed. These floating particles comprise a plurality of cork granules each substantially covered with the plaster containing the larvicidal micro-organism. These particles will float indefinitely. As the plaster dissolves or erodes, the larvicidal micro-organism will be released. After the plaster dissolves, the cork center will continue to float. The cork has a cellular structure, and the cork granules are prepared by a cutting or chopping process. As a result, the external surface of the cork granule has numerous open pockets which capture a mixture of plaster and the larvicidal micro-organism. Thus, as the cork granule continues to float, the larvicidal micro-organism will continually be released. The overall result is a sustained release of the larvicidal micro-organism on the surface of the water where the mosquito larvae breed.

A mixture of plaster and sawdust will not achieve this result, since the sawdust would quickly absorb moisture and sink.

The larvicidal micro-organism comprises spores of bacillus, and the bacillus preferably comprises *Bacillus thuringiensis* Berliner var. *israelensis* and its accompanying proteinaceous parasporal particles which contain protoxin. Other larvicidal micro-organisms which may be feasible, are *Bacillus sphaericus* and aquatic fungi.

These and other objects of the present invention will become apparent from the following specification taken in conjunction with the enclosed drawings.

BRIEF DESCRIPTION OF THE DRAWINGS

FIG. 1 is a top plan view of one embodiment of the disintegratable article (or larvicide carrier) of the present invention.

FIG. 2 is section view thereof, taken along the lines 2—2 of FIG. 1.

FIG. 3 is a schematic view of the article floating freely on the surface of a body of water.

FIG. 4 is a further schematic view of the article, showing the manner in which the flotation of the carrier may be restrained to a given area, if desired.

FIG. 5 is a top plan view of a second (and preferred) embodiment of the present invention.

FIG. 6 is a section view thereof, taken along the lines 6—6 of FIG. 5.

FIG. 7 shows the embodiment of FIG. 5 floating on the surface of a body of water, showing schematically the partial disintegration of the article into a plurality of individual floating particles or "satellite" carriers.

FIG. 8 is an enlarged view of one of the floating "satellites" or particles, taken in section, and showing the cork center substantially covered by the molding plaster, the latter serving as a carrier for the larvicidal micro-organism.

FIG. 9 is an enlarged portion of the external surface of the cork center, showing the plaster with the larvicidal micro-organism received in the numerous pockets on the surface.

FIG. 10 is a schematic showing of the free-floating application of the preferred embodiment of FIG. 5.

FIG. 11 is a schematic showing of a restrained floating application thereof.

FIG. 12 is a schematic showing of a further restrained application, wherein the article is staked to the muddy bottom of a shallow body of water.

DESCRIPTION OF THE PREFERRED EMBODIMENT

With reference to FIGS. 1-4, there is illustrated a first embodiment of the article (or larvicide carrier) 10 of the present invention. Preferably the article 10 is cylindrically shaped and has a slight taper or draft 11, as shown more clearly in FIG. 2. The article is formed from a substantially-uniform homogeneous mixture of cork particles or granules in a molding-type of plaster base. The plaster provides the moldable or compressible base material for the carrier, while the cork (or equivalent material) provides the desired buoyancy. A sufficient proportion of cork particles are added to the mixture to enable the finished carrier to float freely on the surface of a given body of water.

During the mixing process, a desired proportion or concentration of a larvicidal micro-organism is added to the mixture. Preferably, the larvicidal micro-organism includes spores of bacillus, which comprises *Bacillus thuringiensis* Berliner var. *israelensis*, Serotype H-14, and its accompanying proteinaceous parasporal particles which contains protoxin. *Bacillus thuringiensis* Berliner var. *israelensis*, for use against mosquito larvae and black fly larvae, is an aerobic spore-forming rod and can be formulated into either a liquid concentrate or a wettable powder; as previously noted, it is available commercially from Biochem Products under the trademark "BACTIMOS".

As a result, a non-layered unitary article (or larvicidal carrier) is produced solely from the substantially homogeneous mixture of the cork particles and the molding-type of plaster to which the larvicidal micro-organism is added. This molded non-layered unitary article (which has a specific gravity of less than 1.0) is not position sensitive and thus may be thrown out over a body of water in a random fashion without regard for the orientation of the article relative to the surface of the water. This is an important distinction over the layered floating briquet of the prior art (MOSQUITO NEWS) as previously described.

During the mixing process and the formulation of the article, it will be understood by those skilled in the art that suitable precautions are taken to assure that the cork particles will not absorb excess moisture in usage, and that the disintegratable article will remain floating during its useful life. The life span may consist of approximately thirty (30) days, during which time the larvicidal micro-organism will have a sustained release.

An important feature of the present invention is the fact that the base material (which is preferably plaster or gypsum) and the buoyant material (which is preferably cork), as well as the larvicidal micro-organism (which is preferably *B.t.i.*) are all found in nature, are bio-degradable, and are non-toxic to non-target organisms. As a result, there will be no adverse effect rendered to the environment or to the wildlife therein, when the carrier disintegrates (and/or dissolves) in use.

The free-floating application of the article 10 is shown in FIG. 3. As the free-floating article disintegrates, the larvicidal micro-organism will have a sustained release and a widespread distribution on the surface 12 of the body of water 13. This has achieved a quantum improvement in the destruction of the mosquito larvae, many of which feed at or near the surface of the water. In addition, as the larvicidal micro-organism is released, it will gradually settle to the bottom, during which time larvae feeding at different levels will also be destroyed.

Under certain limited circumstances, however, it may be desirable to restrict the free-floating capability of the article to a given area. In catch basins, for example, the article may be removed from the treatment site by a flushing action; and if completely free-floating, could be washed away. Also, in ponds or pools, currents or wind action may move the carrier to one side of the treatment site only. Thus, as shown in FIG. 2, the carrier 10 is provided with a through bore or (central opening during its preparation). Accordingly, the user may attach a string or line 15 to the article 10 by means of a loop and knot 16 as shown in FIG. 4. The other end of the line 15 may be attached to a weight, such as a metal nut 17, to provide an anchor for the carrier. This provides an optional restrained-floating application for the carrier, at the discretion of the user.

The articles of the present invention can also be used for pre-flood treatment. If the articles are applied to dry areas which are known or suspected to become breeding sites when flooded, such as woodland pools and abandoned swimming pools, the articles will float to the surface when flooding occurs and start releasing the active larvicidal material. Alternate wetting and drying will not reduce their effectiveness.

An alternate (and preferred) embodiment of the present invention is illustrated in FIGS. 5-11. The article (or larvicidal carrier) 10' has a substantially-toroidal (or "doughnut") shape. It is relatively-thin (compared to the embodiment of FIGS. 1-4) and is provided with a slight taper, as at 18, and a central bore 19 for a purpose hereinafter described.

When the article 10' floats on the surface of the water 20, as shown in FIG. 7, it gradually disintegrates (dissolves or erodes away) to form a plurality of individual particles or "satellite" carriers 21 which continue to float. This is another important distinction over the sawdust particles resorted to in the prior art. The sawdust particles will quickly absorb moisture and sink; and for that reason, the prior art has resorted to oversized wood blocks to provide an external flotation means.

These floating satellite carriers, as shown in FIG. 8, comprise a cork particle or center 22 surrounded by the molding plaster 23 containing the *B.t.i.* (or other larvicidal micro-organism). The cork particles or granules which are cellular, are formed by a cutting or chopping process. This process results in numerous open "pockets" on the external surface of the cork center, as at 22A in FIG. 9. These pockets become filled with the molding plaster and the *B.t.i.* After the plaster dissolves (and releases the *B.t.i.*) the cork particle 22 continues to float and further releases additional *B.t.i.* entrapped on its external surface. The combination provides a sustained release of the *B.t.i.* over a sufficient period of time (for example thirty days) and over a wide surface area where the mosquito larvae breed in order to achieve an effective mosquito control program.

In lieu of the *B.t.i.*, the larvicidal micro-organism may comprise a *Bacillus sphaericus* or aquatic fungi.

FIGS. 10–12 are schematic illustrations of three respective applications of the article 10' in relatively-shallow bodies of water. FIG. 10 illustrates the free-floating application (similar to FIG. 3 ). FIG. 11 illustrates the restrained-floating application including a string 15' and anchor 17' (similar to FIG. 4 ). FIG. 12 illustrates a further (and more) restrained application, wherein a stake 24 (similar to a surveyor's marking stake and having a length of up to two feet) is used to secure the article 10' to the muddy bottom 25 of the body of water. This allows the article 10' to "ride" up and down on the stake, as indicated by the broken lines, as the water level varies.

The present invention has met with widespread acceptance and immediate recognition by the mosquito control agencies. Indeed, out in the field the articles 10' of the present invention are being referred to as the "mosquito doughnuts". While these "doughnuts" were intended primarily for the myriad of ponds and other small bodies of water generally isolated from one another, it was recently reported that one group is actually throwing them out of helicopters—in lieu of spraying—over a relatively large area. This group is located in Northern Worcester County, Mass.; their responsiblity covers 2000 acres of swamp and 200 acres of ponds, and many of these areas are inaccessible to ground equipment.

These "mosquito doughnuts" of the present invention may be manufactured easily and economically to facilitate widespread usage; they constitute a clean and convenient delivery system, not only for small ponds, but also for relatively large bodies of water; they will remain floating for about thirty days for a sustained release of the larvicidal micro-organism contained therein, thereby assuring an effective mosquito control program without the necessity for repeated applications; means are provided for restrained-floating applications in lieu of a free-floating application, at the option of the mosquito control agency; and all of the ingredients of the present invention are non-toxic, found in nature, and will not affect the environment, the wildlife therein, or the personnel of the mosquito control agency. Thus, a quantum improvement has been achieved, one heretofore not available in the art. Accordingly, the present invention—as contrasted with the abandoned experiments and proposals made in issued patents and other publications in the prior art—has satisfied a long-felt need and has met with substantial commercial success.

Obviously, many modifications may be made without departing from the basic spirit of the present invention. For example, the molding or casting type of plaster (gypsum) and the cork particles or granules are just one example of a base material and a compatible buoyant material, respectively, and it will be understood that various substitutes may be made for a substantially equivalent result consonant with the objects and teachings of the present invention. Accordingly, it will be appreciated by those skilled in the art that within the scope of the appended claims, the invention may be practiced other than has been specifically described herein.

What is claimed is:

1. A floating dispenser for the sustained release of a larvicidal micro-organism consisting of *Bacillus thuringiensis* for the destruction of the larvae of aquatic insects which breed on the surface of a body of water, comprising a unitary substantially homogenous non-layered molded article consisting of a plurality of cork granules, a molding plaster, and the *Bacillus thuringiensis*, wherein the article has a specific gravity of less than 1.0 and may be randomly and conveniently dispensed on to the surface of a body of water without regard for the orientation of the article with respect to the surface of the water, wherein the article will continue to float on the surface of the water where the larvae breen and will gradually disintegrate into a plurality of individual particles which will continue to float for a sustained release of the *Bacillus thuringiensis* and over a relatively wide area of the surface where the larvae breed, and wherein all of the ingredients in the article are non-tosic to non-target organisms and will not adversely affect the environment.

2. The improvement of claim 1, wherein the larvae of the aquatic insects are the larvae of the mosquito and black fly.

3. The improvement of claim 1, wherein the article has a substantially-toroidal slightly-tapered shape and is formed with a central bore, whereby, if desired, the article may be used in a restrained-floating application.

4. The improvement of claim 1, wherein the individual floating particles comprise a plutality of cork granules each substantially covered with the plaster containing the *Bacillus thuringiensis*.

5. The improvement of claim 1, wherein the larvicial micro-organism comprises *Bacillus thuringiensis* Berliner var. *israelensis* and its accompanying proteinaceous particles which contain protoxin.

6. A floating dispenser for the sustained release of a larvicidal micro-organism consisting of *Bacillus thuringiensis* for the destruction of the mosquito or black fly larvae which breed on the surface of a body of water, comprising a unitary substantially homogenous non-layered molded article consisting of a plurality of cork granules, a molding plaster and the *Bacillus thuringiensis*, wherein the article comprises a substantially-toroidal slightly-tapered molded article having a central bore, whereby if desired, the article may be tethered or staked in a restrained-floating application, said larvicidal micro-organism further comprising a *Bacillus thuringiensis* Berliner var. *israelensis* and its accompanying proteinaceous parasporal particles which contain protoxin, wherein the article has a specific gravity of less than 1.0 and may be randomly and conveniently dispensed on to the surface of a body of water without regard for the orientation of the article with respect to the surface of the water, wherein the article will continue to float on the surface of the water and will gradually disintegrate into a plurality of individual floating particles including cork granules substantially covered by the molding-type of plaster containing said larvicidal micro-organism, whereby a sustained release of the larvicidal micro-organism is achieved over a sufficient period of time and over a relatively wide area to destroy the larvae, and wherein all of the ingredients in the article are found in nature and are substantially biodegradable and non-toxic to non-target organisms, and will not adversely affect the environment.

7. A method of dispensing a larvicidal micro-organism consisting of *Bacillus thuringiensis* Berliner var. *israelensis* for the destruction of aquatic insects whose larvae breed on the surface of a body of water, comprising the steps of preparing a substantially homogenous mixture consisting of a molding plaster, *Bacillus thuringiensis* Berliner var. *israelensis*, and cork particles; allowing the homogenous mixture to harden, whereby a unitary floating device with a specific gravity of less than 1.0 is formed for the destruction of the larvae of aquatic insects wherein the larvae breed on the surface of water; manually distributing the article randomly and conveniently onto the surface of a body of water without regard for the orientation of the article with respect to the surface of the water; wherein the article will continue to float on the surface of the water where the larvae breed and will gradually disintegrate into a plurality of individual particles which will continue to float for a sustained release of the larvicidal micro-organism and over a relatively wide area of the surface where the larvae breed, and wherein all of the ingredients in the article are substantially non-toxic to non-target organisms and will not adversely affect the environment.

8. The method of claim 7, further including the step of molding the article into a substantially toroidal shape having a central opening therein.

* * * * *